(12) United States Patent
Jenko

(10) Patent No.: US 7,671,215 B2
(45) Date of Patent: Mar. 2, 2010

(54) PROCESS FOR THE PREPARATION OF COMPOUNDS HAVING AN ACE INHIBITORY ACTION

(75) Inventor: Branko Jenko, Ig (SI)

(73) Assignee: Lek Pharmaceuticals, d.d., Ljubljana (SI)

( * ) Notice: Subject to any disclaimer, the term of this patent is extended or adjusted under 35 U.S.C. 154(b) by 822 days.

(21) Appl. No.: 10/556,986

(22) PCT Filed: May 7, 2004

(86) PCT No.: PCT/SI2004/000021

§ 371 (c)(1),
(2), (4) Date: Sep. 29, 2006

(87) PCT Pub. No.: WO2004/101515

PCT Pub. Date: Nov. 25, 2004

(65) Prior Publication Data

US 2007/0072919 A1    Mar. 29, 2007

(30) Foreign Application Priority Data

May 16, 2003    (SI) .................................. 200300123

(51) Int. Cl.
*C07D 207/00* (2006.01)
*C07D 209/42* (2006.01)
(52) U.S. Cl. ..................................................... 548/492
(58) Field of Classification Search .................. 548/492
See application file for complete search history.

(56) References Cited

FOREIGN PATENT DOCUMENTS

| DE | 289543 | | 5/1991 |
| EP | 1 279 665 | | 1/2003 |
| FR | EP0308341 | * | 2/1989 |
| FR | EP-03008341 | * | 2/1989 |
| WO | WO9725335 | | 7/1997 |
| WO | WO9852923 | | 11/1998 |
| WO | WO0172728 | | 10/2001 |
| WO | 02/094761 | | 11/2002 |
| WO | 02/094857 | | 11/2002 |
| WO | WO03016287 | | 2/2003 |

OTHER PUBLICATIONS

Co-pending U.S. Appl. No. 10/555,848.

* cited by examiner

*Primary Examiner*—Golam M. M. Shameem
*Assistant Examiner*—Susannah Chung
(74) *Attorney, Agent, or Firm*—Arent Fox LLP.

(57) ABSTRACT

The present invention relates to the process for the preparation of compounds of formula (I)

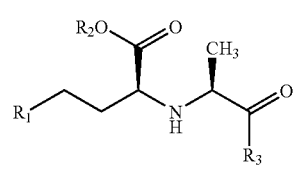

having an ACE inhibitory action wherein carboxy group of stereospecific amino acid is activated with an uranium salt in the presence of an aprotic solvent and an activated amino acid is further transformed with appropriate amine into ACE inhibitor or its precursor.

6 Claims, No Drawings

PROCESS FOR THE PREPARATION OF COMPOUNDS HAVING AN ACE INHIBITORY ACTION

FIELD OF THE INVENTION

The present invention belongs to the field of the organic chemistry synthesis and relates to a process for the preparation of compounds having an ACE inhibitory action.

In particular the present invention relates to the fast, selective and simple process for the preparation of compounds having an ACE inhibitory action.

PRIOR ART

Molecules of most ACE I inhibitors are chemically composed from amino acid and non-amino acid parts. Condensing of these various parts into the final structure are carried out mainly by general reagents for peptide bond formation such as:

phosgene, diphosgene or triphosgene,
carbonyldiimidazole, chlorothionyl imidazole or thionyl diimidazole dicyclohexylcarbodiimide/1-hydroxy benzotriazole.

Different precursors of ACE inhibitors need different coupling agents for the most suitable preparation, good yields and acceptable pharmaceutical quality. For instance SI 94 00 290 describes synthesis of enalapril with thionyl imidazole as coupling agent for formation of peptide bond. This reaction gives good results but very strict reaction conditions control and absolute nonaqueous media is required otherwise side reactions, as for example formation of diketopiperazides etc., are possible and yields drop down.

In another case as described in U.S. Pat. No. 4,914,214 a synthesis between (2S,3aS,7aS)-2-carboxiperhydroindole, wherein carboxy group is protected with benzyl group, and N—((S)-1-carbethoxyibutyl)-(S)-alanine with dicyclohexylcarbodiimide/1-hydroxybenzotriazole as a coupling agent is described in the process of preparing other ACE inhibitor perindopril. This process gives good results but careful isolation is needed due to dicyclohexylurea as a byproduct, which is not easy to separate from reaction mixture. In a later application EP 1 279 665 a process for preparing the same perindopril precursors via acide chlorides by triphosgene is described. This process gives good results but handling with phosgene requires special care.

The aim of this invention is to prepare compounds having an ACE inhibitory action in a new and simple manner, wherein ACE inhibitors are obtained in a high yield and of high purity.

DETAILED DESCRIPTION OF THE INVENTION

Searching for an efficient process for the preparation of ACE I inhibitors we surprisingly found out that the condensation between carboxylic acid and amino group of an appropriate amino acid using uronium salts was fast, smooth and clean.

The reaction itself is very simple and does not require any special conditions. It is very important that it can be finished very fast, e.g. within 15 min, compared to other process for the preparation of ACE inhibitors. In addition, the process of the present invention is higly selective and result in highly pure final product almost without any by-products.

The first embodiment of the present invention is a process for the preparation of compounds having an ACE inhibitory action with formula I:

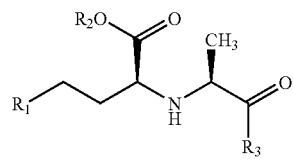

I $R_1$ can be: H, alkyl, phenyl
$R_2$ can be: H, alkyl
$R_3$ can be

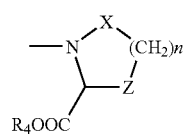

n=1, 2, 3
X, Z=$CH_2$, NH, S
$R_4$=H, M, Me, Et, Pr, Bu, Bz; M=Li, Na, K, Ca or

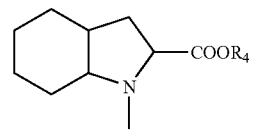

$R_4$=H, Bz, M, Me, Pr, Bu; M=Li, Na, K, Ca or

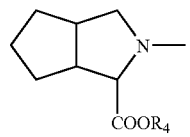

$R_4$=H, Bz, M, Me, Pr, Bu; M=Li, Na, K, Ca or their pharmaceutical acceptable salts, characterised in that carboxy group of stereospecific amino acid with formula II:

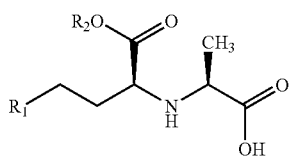

II $R_1$, $R_2$ as above, is activated with uronium salt reagent of the formula III:

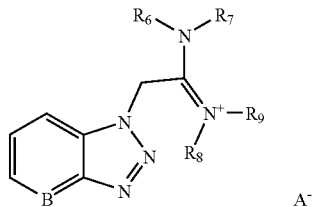

III

B=CH, N; A-=$PF_6$, $BF_4$, $X^-$ (X=halogen)

$R_6$, $R_7$=Me, Me; Et; Et; 1,4-butylene $R_8$, $R_9$=Me, Me; Et; Et; 1,4-butylene in the presence of an aprotic solvent and then activated acid is transformed into peptide with appropriate amine from series $HR_3$ where $R_3$ is:

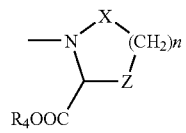

n=1, 2, 3

X, Z=$CH_2$, NH, S $R_4$=H, Bz, M, Me, Pr, Bu; M=Li, Na, K, Ca or

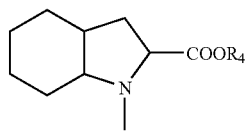

$R_4$=H, Bz, M, Me, Pr, Bu; M=Li, Na, K, Ca or

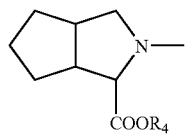

$R_4$=H, Bz, M, Me, Pr, Bu; M=Li, Na, K, Ca

The product thus formed may be transferred into an active pharmaceutical ingredient by transformations of prepared intermediates applying the reactions of removing of protecting groups, cleavage of appropriate esters, neutralizing, alkalizing, acidifying and a pharmaceutically acceptable salt formation if needed.

The uronium salt of formula

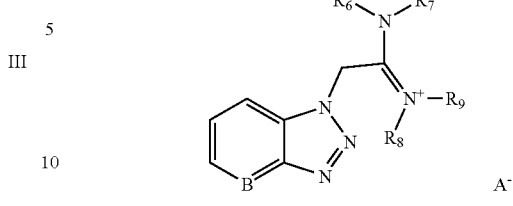

may be selected from the group consisting of:

O-(benzotriazol-1-yl)-N,N,N',N'-tetramethyluronium hexafluorophosphate,

O-(benzotriazol-1-yl)-N,N,N',N'-tetramethyluronium tetrafluoroborate, and

O-(7-azabenzotriazol-1-yl)-N,N,N',N'-tetramethyluronium hexafluorophosphate.

Above mentioned reagents are known from literature (G. A. Grant, Synthetic Peptides, Oxford University Press, 1992, 119) as excellent reagents for the synthesis of peptides without side reactions of isomerisation on chiral centers. These reagents have been mostly applied for coupling of various amino acids but have not been used for the preparation of ACE inhibitors, which are a non-peptide type molecule, yet.

In the another embodiment of the present invention coupling of an acid and the uronium reagent can be carried out by the addition of an organic base such a tertiary amine in 1.5 to 3-molar excess to reagent, preferably 2-molar excess. The tertiary amine may be selected form the group consisting of triethylamine, N,N-diisopropylethylamine, pyridine, lutidine.

Solvents for this type of reactions may be selected from the group consisting of chlorinated hydrocarbons, e.g. methylene chloride, chloroform, cyclic or acyclic-hydrocarbons, esters of organic acids, e.g ethyl acetate, amide solvents, e.g. N,N-dimethylformamide, N,N-dimethylacetamide, N-methylpyrrolidone or other aprotic solvents such as acetonitrile.

A reaction of peptide bond forming is described as follows:

Stochiometric amounts of acid and amine or amounts in the ratio between 1.1:1 to 1:1.1 are reacted together with the above mentioned peptide coupling reagents O-(benzotriazol-1-yl)-N,N,N',N'-tetramethyluronium hexafluorophosphate or tetrafluoroborate in 1 to 1.5-molar excess in the presence tertiary amine in a suitable solvent for 10 to 120 min, preferably from 10 to 45 min and most preferably from 15 to 30 minutes at temperatures from 0 to 40° C., preferably at room temperature, for example 20-25° C. Water is added to reaction mixture and product is isolated by adding a suitable solvent in which product is not soluble.

After washing extracts with water and evaporating of solvent product having good chemical and optical purity is isolated with high yield (87-95%).

Reaction scheme:

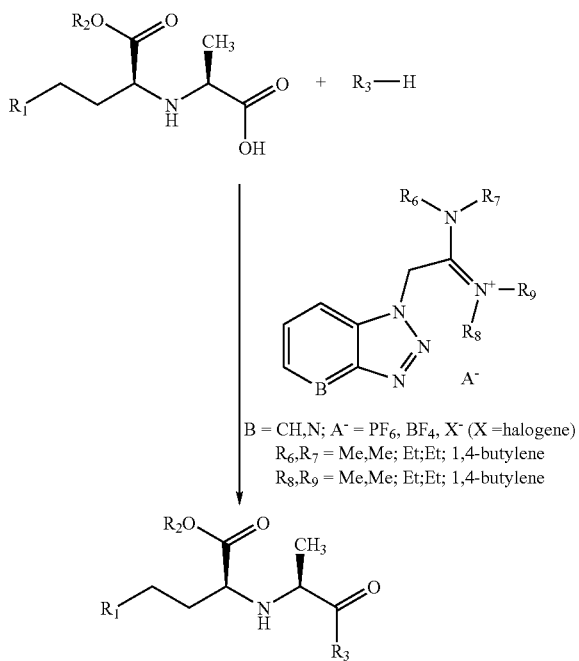

B = CH,N; A⁻ = PF₆, BF₄, X⁻ (X =halogene)
R₆,R₇ = Me,Me; Et;Et; 1,4-butylene
R₈,R₉ = Me,Me; Et;Et; 1,4-butylene The present invention is illustrated by the following examples which do not limit the scope of the invention:

EXAMPLE 1

Preparation of Enalapril Maleate 2.9 ml triethylamine was added to the mixture of 2.79 g of 1-((S)—N-(1-(ethoxycarbonyl)-3-phenylpropyl)-L-alanine and 1.15 g of L-proline in 100 ml of acetonitrile and 5 ml DMF and during stirring 3.8 g O-(benzotriazol-1-yl)-N,N,N',N'-tetramethyluronium hexafluorophosphate was added. The reaction mixture was stirred for further 30 minutes at room temperature. 300 ml of saturated NaCl solution was added and the mixture was extracted twice with 100 ml of ethyl acetate. Combined extracts were washed with 70 ml of water/1 ml of conc. HCl mixture and then with 130 ml of water, dried with Na₂SO₄ and evaporated at 40° C. in vacuum. 3.55 g of enalapril was obtained.

The intermediate was dissolved in 100 ml of ethyl acetate, then a solution of 1.00 g of maleic acid in 50 ml of ethyl acetate was added and after 30 minutes of stirring enalapril maleate is filtered off, dried in vacuum at 40° C. obtaining 4.2 g of product (85.4%).

EXAMPLE 2

Preparation of benzyl (2S,3aS,7aS)-((2-(1-(ethoxycarbonyl)-(S)-butylamino)-(S)-propionyl)octahydroindole-2-carboxylate (benzyl ester of perindopril)

Mixture of 855 mg of benzyl ester of (2S,3aS,7aS)-2-carboxyperhydro indole, 651 mg of N-((S)-1-carbethoxybutyl)-(S)-alanine and 1137 mg of O-(benzotriazol-1-yl)-N,N,N',N'-tetramethyluronium hexafluorophosphate and 0.84 ml of triethylamine was stirred in 20 ml of acetonitrile for 30 minutes. 50 ml of saturated NaCl was added and product was extracted twice with 35 ml of EtOAc. Combined extracts were washed with 70 ml of water/1 ml of conc. HCl and than with 130 ml of waters dried with Na₂SO₄ and evaporated at 40° C. in vacuum. 1210 mg (87.7%) of benzyl (2S,3aS,7aS)-((2-(1-(ethoxycarbonyl)-(S)-butylamino)-(S)-propionyl)octahydroindole-2-carboxylate (benzyl ester of perindopril) was obtained.

The obtained product is a precursor for preparing perindopril or perindopril erbumin what can be done by the methods from literature, for example transformed into free acid and than into pharmaceutically acceptable salt by known methods described in U.S. Pat. No. 4,914,214.

EXAMPLE 3

Preparation of Trandolapril

To 2.79 g of (S)-1-(N-(1-(ethoxycarbonyl)-3-phenylpropyl)-L-alanine and 1.75 g of (2S,3aR,7aS)-octahydro-1H-indol-2-carboxylic acid in 100 ml of acetonitrile and 5 ml DMF first 2.9 ml of triethylamine and then with stirring 3.8 g O-(benzotriazol-1-yl)-N,N,N',N'-tetramethyluronium hexafluorophosphate were and the stirring of the mixture was continued for 30 minutes at room temperature. Finally, 300 ml of saturated NaCl solution was added and the mixture was extracted twice with 100 ml of ethyl acetate. After isolation of the product, which was done by the same way as in example 1, 3.96 g (92%) of trandolapril was obtained.

The invention claimed is:
1. A process for the preparation of perindopril:

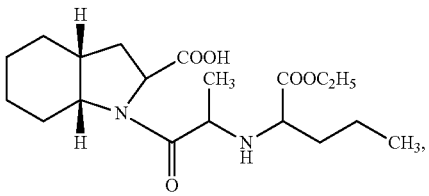

comprising reacting 1-((S)—N-(1-(ethoxycarbonyl)-3-phenylpropyl)-L-alanine and (2S,3aR,7aS)-octahydro 1H-indole-2-carboxylic acid or its ester with a uronium salt selected from the group consisting of: O-(benzotriazol-1-yl)-N,N,N',N'-tetramethyluronium hexafluorophosphate and O-(benzotriazol-1-yl)N,N,N',N'-tetramethyluronium tetrafluoroborate, in the presence of a tertiary amine in an aprotic solvent.

2. The process according to claim 1, wherein the amounts of 1-((S)—N-(1-(ethoxycarbonyl)-3-phenylpropyl)-L-alanine and (2S,3aR,7aS)-octahydro-1H-indole-2-carboxylic acid or its ester are in the ratio between 1.1:1 to 1:1.1.

3. The process according to claim 1, wherein the uronium salt is O-(benzotriazol-1-yl)-N,N,N',N'-tetramethyluronium hexafluorophosphate.

4. The process according to claim 1, wherein the tertiary amine is triethylamine.

5. The process according to claim 1, wherein the aprotic solvent is acetonitrile.

6. The process according to any one of claims 1-5, comprising a further step of reacting the obtained perindopril with t-butylamine to provide perindopril erbumine.

* * * * *